United States Patent
Rimando et al.

(10) Patent No.: US 9,439,875 B2
(45) Date of Patent: Sep. 13, 2016

(54) ANXIOLYTIC EFFECT OF PTEROSTILBENE

(75) Inventors: Agnes M. Rimando, Oxford, MS (US); Abir El-Alfy, Frankfort, IL (US); Md Al Rahim, Baltimore, MD (US)

(73) Assignees: The United States of America, as represented by The Secretary of Agriculture, Washington, DC (US); University of Mississippi, University, MS (US)

( * ) Notice: Subject to any disclaimer, the term of this patent is extended or adjusted under 35 U.S.C. 154(b) by 214 days.

(21) Appl. No.: 13/105,470

(22) Filed: May 11, 2011

(65) Prior Publication Data

US 2016/0067192 A1   Mar. 10, 2016

(51) Int. Cl.
| | |
|---|---|
| *A61K 31/09* | (2006.01) |
| *A61P 25/22* | (2006.01) |
| *A61K 31/075* | (2006.01) |
| *A61K 31/045* | (2006.01) |

(52) U.S. Cl.
CPC ........... *A61K 31/075* (2013.01); *A61K 31/045* (2013.01)

(58) Field of Classification Search
None
See application file for complete search history.

(56) References Cited

FOREIGN PATENT DOCUMENTS

NL   WO2010/095493   *   8/2010   .............   A61K 31/05

OTHER PUBLICATIONS

PanLab Open Field Test in www.panlab.com/panlabWeb/Software/SMART%20JUNIOR/pdfProtocols/AS%20Open%20Field%20with%20smart%20JUNIOR.pdf.*

Sonmez et al. in Neuroscience Letters 420 (2007) 133-137.*
Johnson T.D. in Life Extension Magazine "The Other Resveratrol" 2009 (www.lifeextension.com/magazine/2009/ss/the-other-resveratrol/page-01) (retrieved from the internet Jul. 20, 2015).*
Prut et al. in European Journal of Pharmacology 463, 3-33 (2003).*
Chang et al. in Neurobiology of Aging 33, 2062, 2071 (2012).*

* cited by examiner

*Primary Examiner* — Dennis Heyer
(74) *Attorney, Agent, or Firm* — John D. Fado; Evelyn M. Rabin (57) ABSTRACT

We report for the first time that pterostilbene, a natural analog of resveratrol, shows anxiolytic-like action by down-regulating phosphorylated levels of ERKs in the hippocampus of mice. Mice administered pterostilbene (1-10 mg/kg BW) by oral gavage were subjected to the Elevated-plus maze (EPM) test. Pterostilbene manifested anxiolytic activity at 1 and 2 mg/kg doses, demonstrated by an increase in percent permanence time and number of entries in open arms, critical determinants correlated with anxiety. This anxiolytic activity of pterostilbene was comparable to that of diazepam at 1 and 2 mg/kg in the EPM. The percent traveled distance and the percent permanence time in the enclosed arms were decreased with the 1 and 2 mg/kg doses. The 5 and 10 mg/kg doses did not show any anxiolytic effect. Locomotor activity was unaffected in all doses. Western blot analysis corroborated the observed behaviors in the EPM, revealing a decrease in both ERK1 and ERK2 phosphorylation in hippocampal homogenates from mice treated with 1 and 2 mg/kg doses; the 5 and 10 mg/kg doses showed no significant effect on the phosphorylation of ERKs. Pterostilbene was detected in serum and brain tissue following a single oral administration, demonstrating that the compound can cross the blood-brain barrier to reach the brain regions, including hippocampus, and thereby exert its anxiolytic effect. Resveratrol, the parent molecule of pterostilbene, did not have any anxiolytic effect.

9 Claims, 6 Drawing Sheets

ANXIOLYTIC EFFECT OF PTEROSTILBENE

BACKGROUND OF THE INVENTION

1. Field of the Invention

This invention relates to a method for treating, alleviating or preventing anxiety by administering a pharmaceutical composition comprising a therapeutically effective amount of pterostilbene, an analog of resveratrol, found in grapes and some *Vaccinium* berries.

2. Description of the Relevant Art

Anxiety disorders are common in community settings and in primary and secondary medical care, and frequently turn into chronic clinical conditions (Nutt et al. 2002. *Int. J. Neuropsychopharmacol.* 5:315-325). Anxiety disorders are the most common type of psychiatric disorders, with an incidence of 18.1% and a lifetime prevalence of 28.8% (Kessler et al. 2005. *Arch. Gen. Psychiatry* 62: 617-627; Ohayon, M. M. 2006. *J. Psychiatr. Res.* 40: 475-476). Anti-anxiety drugs have been used by human beings for thousands of years. Benzodiazepine group of drugs are fast acting, effective and the most commonly prescribed anxiolytics (Bandelow et al. 2008. *World J. Biol. Psychiatry* 9:248-312; Baldwin et al. 2005. *J. Psychopharmacol.* 19:567-596; Rudolph and Mohler. 2006. *Curr. Opin. Pharmacol.* 6:18-23). However, their long-term use is associated with side effects such as sedation, development of tolerance, abuse liability, and withdrawal symptoms (Nutt et al., supra; Bandelow et al., supra; Baldwin et al., supra). Currently, a selective serotonin reuptake inhibitor group of antidepressants is used as a first-line treatment for most anxiety disorders. However, this group also has drawbacks. In particular, there is a slow onset of therapeutic action, thus several weeks of treatment are required for the anxiolytic effects to occur (Nutt et al., supra; Bandelow et al., supra; Baldwin et al., supra). Therefore, there is still a need for anxiolytic compounds that have rapid therapeutic action but are devoid of untoward effects.

Large numbers of natural compounds have provided not only useful pharmacological tools (Furukawa etal. 1993. *J. Biol. Chem.* 268:26026-26031), but also potential therapeutic leads for drug development (Liu, J. 1993. *Trends Pharmacol. Sci.* 14:182-188). Stilbenes are a group of phytochemicals having an $\alpha$, $\beta$-diphenylethylene core structure. Stilbenes have been reported in a large number of unrelated plant genera including grapes; peanuts, and *Vaccinium* berries (Chong et al. 2009. *Plant Sci.* 177:143-155). Resveratrol, a widely studied stilbene, has been reported to exert anti-oxidant, anti-inflammatory, chemopreventive, and anti-aging effects in a number of biological systems (Aggarwal et al. 2004. *Anticancer Res.* 24:2783-2840; Baur and Sinclair. 2006. *Nat. Rev. Drug Disco.* 5:493-506; Bishayee, A. 2009. *Cancer Prev. Res.* 2:409-418). Recently, pterostilbene, a natural analog of resveratrol, found in some *Vaccinium* berries such as blueberries and deerberries (Rimando et al. 2004. *J. Agric. Food Chem.* 52:4713-4719) has been receiving much attention for having diverse effects like those shown for resveratrol. Pterostilbene has analgesic, antidiabetic, antioxidant, anti-inflammatory, hypolipidemic, and cancer chemopreventive properties (Amarnath Sateesh and Pari. 2006. *J. Pharm. Pharmacol.* 58:1483-1490; Remsberg et al. 2008. *Phytotherapy Res.* 22: 169-179; Rimando et al. 2002. *J. Agric. Food Chem.* 50:3453-3457; Rimando et al. 2005. *J. Agric. Food Chem.* 53:3403-3407). Pterostilbene also has significant effect on colon cancer development (Paul et al. 2009. *Cancer Prev. Res.* 2:650-657), invasion and metastasis (Pan et al. 2009. *Carcinogenesis* 30:1234-1242), and in reversing cognitive deficits in aged rats (Joseph et al. 2008. *J. Agric. Food Chem.* 56:10544-10551). However, the anxiolytic potential of pterostilbene has not yet been investigated.

Many natural compounds, including stilbenes, interact with protein kinases involved in different signaling pathways such as inducible nitric oxide synthase (iNOS), cyclooxygenase-2 (COX-2), and p38 mitogen-activated protein kinase (MAPK) (Paul et al. 2009, supra). It is well established that extracellular signal-regulated kinase 1/2 (ERK 1/2), a member of the MAPK family, plays an important role in transcriptional regulation in many cell types, including neurons (Hetman and Gozdz. 2004. *Eur. J. Biochem.* 271:2050-2055). Accumulating evidence indicates that the ERK signaling pathway is activated under various stimuli (Davis, R. J. 1993. *J. Biol. Chem.* 268:14553-14556; Hetman and Gozdz, supra), including exposure to stress (Gerrits et al. 2006. *Neuroscience* 142:1293-1302). In addition, the ERK signaling pathway in the hippocampal and lateral amygdala is speculated to play a role in anxiety (Paul et al. 2007. *Biol. Psychiatry* 61:1049-1061; Tronson et al. 2007. *Neuropsychopharmacol.* 133:1570-1583). This notion is further consolidated by the findings that the levels of phophorylated ERK increased significantly during anxiety. Therefore, the ERK signal transduction pathway might play an important role in anxiety and its inhibition could produce anxiolytic effects (Ailing et al. 2008. *J. Psychiatr. Res.* 43:55-63).

Thus, in view of the role of signaling pathways in anxiety and the need for agents which can be used to treat anxiety, the goal of this work was to determine the effects of pterostilbene as an inhibitor of anxiety.

SUMMARY OF THE INVENTION

We have investigated the property of pterostilbene as an inhibitor of anxiety and have determined that pterostilbene can be used as an anti-anxiety agent.

In accordance with this discovery, it is an object of the invention to provide method for treating, alleviating or preventing anxiety in a subject in need thereof by administering a therapeutically effective dose of pterostilbene, its pharmaceutically acceptable salts or isomers thereof.

Also part of this invention is a kit, comprising a pharmaceutical composition containing pterostilbene; and instructions for the use of the kit.

Other objects and advantages of this invention will become readily apparent from the ensuing description.

BRIEF DESCRIPTION OF THE DRAWINGS

FIGS. 5A and 5B depict the effect of oral administration of pterostilbene on phosphorylation of ERK1/2 in the hippocampus. FIG. 5A shows representative data on phosphorylated ERK1/2 levels for mice sacrificed immediately after EPM test. FIG. 5B shows the densitometric analysis of the changes in ERK 1/2 phosphorylation for mice sacrificed immediately after training. Values are expressed as the mean±SEM of at least three animals. *p<0.05, **p<0.01 compared to vehicle control (one-way ANOVA followed by Dunnett's test).

DETAILED DESCRIPTION OF THE INVENTION

Like resveratrol, a multitude of pharmacological activities have also been attributed to pterostilbene. Our present work adds to the string of health-beneficial properties reported for pterostilbene; here, we demonstrate its anxiolytic effects for the first time. In the present study, the anxiolytic-like effect of pterostilbene was investigated on the classic animal model of anxiety, the elevated plus-maze (EPM), a behavioral model for anxiolysis assessment. The EPM test is considered one of the most widely validated tests for assaying new anxiolytic agents (Pellow et al. 1985. *J. Neurosci. Methods* 14: 149-167; Hogg, S. 1996. *Pharmacol. Biochem. Behav.* 54: 21-30). Diazepam, one of the most frequently used anxiolytic compounds was used as a positive control in this study. Given the conflict displayed by rodents between the drive to explore a new environment and the fear of an open elevated place, the EPM is a widely used model of anxiety employed by a large number of investigators (Pellow et al., supra; Hogg, supra). It has been proposed that normal exploratory behavior of rodents-is in-favor of the enclosed arms of the maze in the elevated plus-maze model, and that aversion towards the anxiety-provoking open arms is the basis of EPM model (Pellow et al., supra; Ohl, F. 2003. *Clin. Neruosci. Res.* 3:233-238). A large body of evidence has established that the administration of anxiolytic compounds reduces the natural aversion to the open arms and promotes the exploration thereof (Pellow et al., supra; Hogg, supra).

In our studies, we also determined the plasma and tissue levels of pterostilbene after oral administration of the compound to mice. The serum levels of pterostilbene increased with dose and corresponding increases in the hippocampal levels of pterostilbene were observed (See Experiment 5). Changes of phosphorylated ERK1/2 in the hippocampus of mice were measured with the further aim to study the effects on protein kinase regulation and to elucidate the underlying mechanisms of pterostilbene action.

Pterostilbene manifested anxiolysis at 1 and 2 mg/kg doses: the percent Permanence Time in Open Arms (PTOA), and Number of Entries in Open Arms (NEOA), which are critical determinants and considered to be correlated with anxiety, were increased at defined low doses (See Example 2). Pterostilbene was also able to increase the percent Traveled Distance in Open Arms (TDOA) at both 1 and 2 mg/kg doses. However, higher doses (5 and 10 mg/kg) didn't show any anxiolytic effect; and contrarily, the higher doses had the tendency to increase the aversion towards the open arms, i.e. the higher doses were anxiogenic. The anxiolytic activity of pterostilbene was further corroborated with findings that the percent Traveled Distance in the Enclosed Arms (TDEA) and the percent Permanence Time in the Enclosed Arms (PTEA) also decreased upon treatment with 1 and 2 mg/kg of pterostilbene. Also, the anxiolytic activity of pterostilbene was quite similar to that of diazepam. The 2 mg/kg of pterostilbene showed comparable effects to 2 mg/kg of diazepam, at least, in the EPM. The use of diazepam as a positive control, thus, further confirms the anxiolytic potential of pterostilbene in EPM behavioral paradigm. The Number of Entries in the Enclosed Arms (NEEA), being a purer measure of locomotor activity as it changes independently of NEOA and PTOA, was unaltered across the dose range used in this experiment. It is worth mentioning that resveratrol, the parent molecule of pterostilbene, did not have any anxiolytic effect, tested at doses of 3 and 20 mg/kg (Patisaul et al. 2009. *Hormones and Behavior* 55:319-328).

The locomotor activity of the animals was evaluated to demonstrate that the anxiolytic activity of pterostilbene at lower doses (1 and 2 mg/kg) was not a secondary consequence of depressive action of the compound on the motor activity of the animals. The absence of anxiolytic effect at the higher doses (5 and 10 mg/kg) was also not due to motor impairment. Therefore, no stimulant or depressive actions were recorded, suggesting that it is very unlikely that the observed anxiolytic effects are false positives.

In addition to the EPM and locomotor tests, we also focused on molecular substrates that could explain the observed anxiolytic-like action of pterostilbene by studying expression of proteins that have a role in anxiety. Results obtained in Western blot studies showed a marked reduction of the phosphorylated ERK1 levels in the hippocampus of animals treated with those low doses (1 and 2 mg/kg) of pterostilbene which demonstrated anxiolytic effects in EPM. A mild decrease in the phosphorylation state of ERK2 in the hippocampus at the same doses was also observed. Importantly, the inability of the higher doses (5 and 10 mg/kg) to cause any change in the phosphorylation state of ERK 1/2 is consistent with the lack of anxiolytic effect of the compound observed in EPM at the same doses. In addition, three genes in the Akt family (Akt1, Akt2, and Akt3) code for enzymes that are members of the serine/threonine-specific protein kinase family (EC 2.7.11.1) and our analysis showed that there was no change in the levels of phosphorylated Akt in the hippocampus of animals. Therefore, our results suggest a correlation between anxiolytic action of pterostilbene and its capacity to decrease ERK activity in the hippocampus of mice. Other studies have shown that pterostilbene block the activation of ERK1/2 in RAW 264.7 cells (Pan et al. 2008. *J. Agric. Food Chem.* 56: 7502-7509). Our study is the first to demonstrate in vivo that particular low doses of pterostilbene down-regulate activation of ERK1/2.

Recent reports indicate that levels of pERK in different brain regions, including hippocampus and prefrontal cortex (PFC), increase significantly during anxiety, and its inhibition could yield anxiolytic-like actions (Ailing et al., supra; Martinez et al. 2009. *Pharmacol. Biochem. Behav.* 92:291-296). This fact is in agreement with the observed anxiolytic-like activity of the green tea polyphenolic compound epigallocatechin-3-gallate after acute administration in mice (Vignes et al. 2006. *Brain Res.* 1110:102-115), and that this compound also has ability to decrease the phosphorylation state of ERK1/2 (Chung et al., 2001. *FASEB J.* 15: 2022-2024; Sah et al. 2004. *J. Biol. Chem.* 279:12755-12762). Furthermore, it had been reported that sustained nuclear accumulation of pERK1/2 was described as an event with harmful consequences (Colucci-D'Amato et al. 2002. *Bioessays* 25:1085-1095). Increased pERK1/2 signal transduction after chronic stress was prevented by cyclic 17β-estradiol administration in limbic structures, which might protect against the harmful consequences of recurrent stress (Gerrits et al., supra). More encouragingly, inhibition of the ERK pathway using MEK inhibitors had also shown therapeutic effects against damage of various organs (Otani et al. 2007. *J. Clin. Neurosci.* 14:42-48).

The brain contains a variety of receptors like NMDA, GABA and ion channels that can potentially alter the phosphorylation of MAP kinase. Studies showing the activation of MAP kinase by NMDA receptors have been well documented (Xia et al. 1996. *J. Neurosci.* 16:5425-5436; Orban et al. 1999. *Trends Neurosci.* 22:38-44). Also, studies implicated the ERK/MAPK pathway as a negative modulator of GABA receptor function (Bell-Homer et al. 2006. *J. Neurobiol.* 66:1467-1474). Whether the decrease in ERK1/2 phosphorylation is mediated by blockade of NMDA receptors or activation of GABA receptors, is a subject of our ongoing investigation.

Given that pterostilbene at higher doses did not significantly alter locomotor activity or cause a significant reduction, one might argue why the compound at higher doses failed to exhibit any anxiolytic-like action in the EPM test. When a rodent explores a novel environment (EPM being the novel environment here) the capacity of the working memory buffer may come into play, at least in part, even though EPM is not purely a behavioral paradigm. Spatial learning is also important for the animals to recognize the location of open and enclosed arms in the EPM, and that acquisition of spatial information is dependent on hippocampal function (Olton and Papas. 1979. *Neuropsychologia* 17:669-682). Thus, there is a possibility that the initial EPM experience might modify the ensuing behavior of the mice in the same maze-session in relation to time. Moreover, high dose pterostilbene (10 mg/kg) could improve the cognitive performance, particularly spatial memory in rats (Joseph et al., supra). Indeed, we found in our study that at 10 mg/kg dose the level of pterostilbene was 1.1217 ng/hippocampus (Table 2), similar to that reported by Joseph et al., supra). Therefore, it is reasonable to speculate that pterostilbene at high doses (5 and 10 mg/kg), acting simultaneously on memory pathways, may have increased the capacity of working memory buffer of the mice, thereby limiting their exploratory behavior towards the stress-provoking, aversive open arms after their very initial exposure to the arms in the EPM. This notion is further strengthened by the findings that pterostilbene at high doses increased the level of phosphorylated ERKs in the hippocampus as compared to the lower doses suggesting enhanced pERK levels may have played a role in increasing the working memory buffer.

Our results demonstrated, for the first time, that pterostilbene, a constituent of blueberries, showed anxiolytic-like action in elevated plus-maze in mice. Also, higher doses of pterostilbene did not show any sedating tendency in EPM and locomotor activity monitoring chambers, suggesting favorable side-effect profile of the compound. The anxiolytic activity of the compound was accompanied by the down-regulation of ERK1/2 phosphorylation in the hippocampus of the animals. However, future studies would be required to better understand the mechanisms through which pterostilbene downregulates ERK phosphorylation.

The compounds of the present invention are therefore of use to treat, alleviate, or prevent anxiety in a subject in need thereof. In a special embodiment, the compounds of the invention are considered useful for the treatment, prevention or alleviation of anxiety disorders, such as panic disorder with or without agoraphobia, agoraphobia without history of panic disorder, animal and other phobias including social phobias, obsessive-compulsive disorder, and generalized or substance-induced anxiety disorder; stress disorders including post-traumatic and acute stress disorder; sleep disorders; memory disorder; neuroses; convulsive disorders, for example epilepsy, seizures, convulsions, or febrile convulsions in children; migraine; mood disorders; depressive or bipolar disorders, for example depression, single-episode or recurrent major depressive disorder, dysthymic disorder, bipolar disorder, bipolar I and bipolar II manic disorders, and cyclothymic disorder, psychotic disorders, including schizophrenia; neurodegeneration arising from cerebral ischemia; attention deficit hyperactivity disorder; pain and nociception, e.g. neuropathic pain; emesis, including acute, delayed and anticipatory emesis, in particular emesis induced by chemotherapy or radiation; motion sickness, post-operative nausea and vomiting; eating disorders including anorexia nervosa and bulimia nervosa; premenstrual syndrome; neuralgia, e.g. trigeminal neuralgia; muscle spasm or spasticity, e.g. in paraplegic patients; the effects of substance abuse or dependency, including alcohol withdrawal; cognitive disorders, such as Alzheimer's disease; cerebral ischemia, stroke, head trauma; tinnitus: and disorders of circadian rhythm, e.g. in subjects suffering from the effects of jet lag or shift work.

A composition in accordance with the present invention containing pterostilbene, or a pharmaceutically acceptable salt of pterostilbene, can be prepared by conventional procedures for blending and mixing compounds. Preferably, the composition also includes an excipient, most preferably a pharmacuetical excipient. Compositions containing an excipient and incorporating the pterostilbene can be prepared by procedures known in the art. For example, pterostilbene can be formulated into tablets, capsules, powders, suspensions, solutions for oral administration and solutions for parenteral administration including intravenous, intradermal, intramuscular, and subcutaneous administration, and into solutions for application onto patches for transdermal application with common and conventional carriers, binders, diluents, and excipients.

While a chemical compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the chemical compound of the invention, or a pharmaceutically acceptable salt or derivative thereof, together with one or more pharmaceutically acceptable carriers, and, optionally, other therapeutic and/or prophylactic ingredients, known and used in the art. The carrier(s) must be "acceptable" in the sense of being compatible with the other ingredients of the formulation and not harmful to the recipient thereof.

Pharmaceutical compositions of the invention may be those suitable for oral, rectal, bronchial, nasal, pulmonal, topical (including buccal and sub-lingual), transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

The chemical compound of the invention, together with a conventional adjuvant, carrier, or diluent, may thus be placed into the form of pharmaceutical compositions and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The chemical compound of the present invention can be administered in a wide variety of oral and parenteral dosage forms. It will be obvious to those skilled in the art that the following dosage forms may comprise, as the active component, either a chemical compound of the invention or a pharmaceutically acceptable salt of a chemical compound of the invention.

For preparing pharmaceutical compositions from a chemical compound of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid, which is in a mixture with the finely divided active component. In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

Liquid preparations include solutions, suspensions, and emulsions, for example, water or water-propylene glycol solutions. For example, parenteral injection liquid preparations can be formulated as solutions in aqueous polyethylene glycol solution. The chemical compound according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or, by lyophilization from solution, for constitution with a suitable vehicle, e.g. sterile, pyrogen-free water, before use.

Aqueous solutions suitable for oral use can be prepared by dissolving the active component in water and adding suitable colorants, flavors, stabilizing and thickening agents, as desired. Aqueous suspensions suitable for oral use can be made by dispersing the finely divided active component in water with viscous material, such as natural or synthetic gums; resins, methylcellulose, sodium carboxymethylcellulose, or other well known suspending agents.

For topical administration to the epidermis the chemical compound of the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or coloring agents.

Compositions suitable for topical administration in the mouth include lozenges comprising the active agent in a flavored base, usually sucrose and *acacia* or tragacanth; pastilles comprising the active ingredient in an inert base such as gelatin and glycerine or sucrose and *acacia;* and mouthwashes comprising the active ingredient in a suitable liquid carrier.

Solutions or suspensions are applied directly to the nasal cavity by conventional means, for example with a dropper, pipette or spray. The compositions may be provided in single or multi-dose form. In compositions intended for administration to the respiratory tract, including intranasal compositions, the compound will generally have a small particle size for example of the order of 5 microns or less. Such a particle size may be obtained by means known in the art, for example by micronization.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

Tablets, capsules and lozenges for oral administration and liquids for intravenous administration and continuous infusion are preferred compositions. Solutions or suspensions for application to the nasal cavity or to the respiratory tract are preferred compositions. Transdermal patches for topical administration to the epidermis are preferred.

Further details on techniques for formulation and administration may be found in the latest edition of Remington's Pharmaceutical Sciences (Maack Publishing Co., Easton, Pa.).

In another aspect the invention provides a method for the treatment, prevention or alleviation of anxiety in a subject in need thereof, and which method comprises administering to such a subject, including a human, in need thereof an effective amount of the pterostilbene of the invention.

A therapeutically effective dose refers to that amount of active ingredient, which ameliorates the symptoms or condition. Therapeutic efficacy and toxicity, e.g. $ED_{50}$ and $LD_{50}$, may be determined by standard pharmacological procedures in cell cultures or experimental animals. The dose ratio between therapeutic and toxic effects is the therapeutic index and may be expressed by the ratio $LD_{50}/ED_{50}$. Pharmaceutical compositions exhibiting large therapeutic indexes are preferred.

The dosage of compounds used in accordance with the invention varies depending on the compound and the condition being treated. The age, lean body weight, total weight, body surface area, and clinical condition of the recipient patient; and the experience and judgment of the clinician or practitioner administering the therapy are among the factors affecting the selected dosage. Other factors include the route of administration, the patient's medical history, the severity of the disease process, and the potency of the particular compound. The dose should be sufficient to ameliorate symptoms or signs of the disease treated without producing unacceptable toxicity to the patient. The dosage may be varied by titration of the dosage to the particular circumstances of this invention to produce the desired therapeutic effect.

Appropriate conversion of drug doses from animal studies to human studies (human equivalent dose, HED) is obtained through the use of the body surface area (BSA) normalization method. The interrelationship of dosages for animals and humans (based on milligrams per meter squared of body surface) is described by Reagan-Shaw et al. (2007. *FASEB J.* 22: 659-661). The formula for dose translation from animal dose to human dose through normalization to BSA (mg/m$^2$) is:

$$HED(\text{mg/kg}) = \text{Animal dose (mg/kg) multiplied by} \frac{\text{Animal } K_m}{\text{Human } K_m}$$

where the $K_m$ factor, body weight (kg) divided by BSA (m$^2$), is used to convert the mg/kg dose used in the animal study to an mg/m$^2$. The $K_m$ factor for mouse is 3 and the $K_m$ factor for human is 37. A table (Table 1, Reagan-Shaw et al., supra) lists $K_m$ factors calculated for several animal species based on data from FDA Guidelines.

The pterostilbene is present in the composition in an amount sufficient to treat, alleviate, or prevent anxiety in a subject in need thereof. In a most preferred embodiment, the pterostilbene is present in the composition in an amount sufficient to treat, alleviate, or prevent anxiety by itself. The active ingredient may be administered in one or several doses per day. A satisfactory result can, in certain instances, be obtained at a dosage as low as the human equivalent dose (HED) of 0.0405 mg/kg p.o. or a dose of about 3 mg/day p.o. for a 60 kg human patient to a dose of about 15 mg/day p.o. for a 60 kg human patient. Given that pterostilbene has a half-life of approximately 2 hr, an appropriate range can be from about 10 mg/day p.o. to about 100 mg/day p.o. for said human patient.

It is at present contemplated that suitable dosage ranges are 10-100 mg daily for human patients, dependent as usual upon the exact mode of administration, form in which administered, the indication toward which the administration is directed, the subject involved and the body weight and body surface area of the subject involved, and further the preference and experience of the physician or veterinarian in charge. When administered in combination with compounds known in the art for treatment of the diseases, the dosing regimen may be reduced.

EXAMPLES

Having now generally described this invention, the same will be better understood by reference to certain specific examples, which are included herein only to further illustrate the invention and are not intended to limit the scope of the invention as defined by the claims.

Example 1

Pterostilbene

Figure 1:
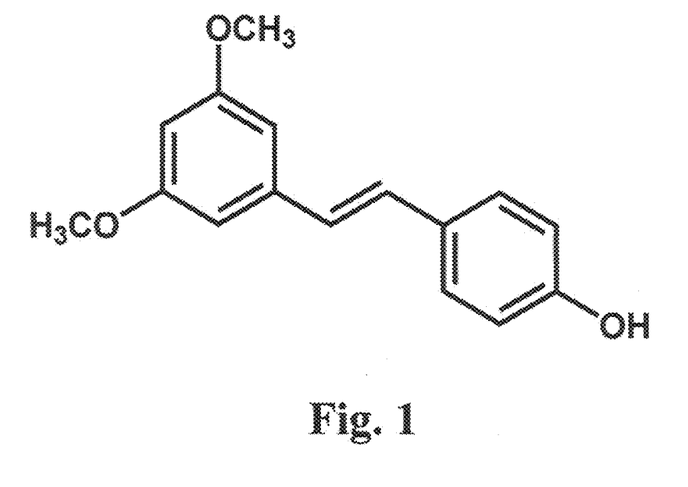
FIG. 1 shows the chemical structure of pterostilbene.

Pterostilbene was synthesized as previously described (Joseph et al., supra). Briefly, pterostilbene was synthesized by condensation of 3,5-dimethoxybenzaldehyde and 4-hydroxyphenylacetic acid in acetic anhydride and triethylamine. The reaction mixture was heated (150° C.) under an atmosphere of nitrogen and continuously stirred. After 20 h, the reaction was stopped and cooled to room temperature, and concentrated hydrochloric acid (5 mL) was added. A precipitate formed, and this was dissolved in 50 mL of chloroform and then extracted with 10% aqueous sodium hydroxide. The aqueous extract was acidified to pH 1 with concentrated hydrochloric acid and stirred for at least 6 h, resulting in the precipitation of the intermediate product, α-[(3,5-dimethoxyphenyl)methylene]-4-hydroxy-(αZ)-benzeneacetic acid. This intermediate product was heated with 1.0 g of copper in 10 mL of quinoline (200° C., 6 h, under nitrogen). The reaction mixture was cooled to room temperature and filtered. To the filtrate was added 5 N hydrochloric acid (25 mL), which Was stirred for 1 h and then extracted with chloroform. The chloroform extract containing impure pterostilbene was purified by flash chromatography on a Horizon HPFC system (Biotage, Inc., Charlottesville, Va.), using a silica gel column and the solvent system ethyl acetate:hexane (linear gradient from 15:85 to 100% ethyl acetate). Fractions containing pure pterostilbene were combined and concentrated in vacuum. Pterostilbene was recrystallized in hexane, and its structure was confirmed from its spectroscopic data (UV, mass spectrometry, and nuclear magnetic resonance spectroscopy) (FIG. 1).

Pterostilbene was dissolved in a mixture of cremophor, ethanol, and saline (1:1:18) in doses between 1 and 10 mg/kg body weight. A volume of 10 mL/kg was administered orally 1 h before the behavioral tests.

Example 2

Effect of Pterostilbene in Murine Elevated Plus-Maze Behavioral Study

Eight-week old male Swiss Webster mice (Harlan, Ind., USA) weighing 24-30 gm at the time of testing were used for all studies. Animals were housed in groups of five, were given food and water ad libitum, and maintained under a 12:12 h day:light cycle. All mice were randomly selected for each treatment group. Housing, handling and experimental procedures were approved by the Institutional Animal Care and Use Committee (IACUC) of the University of Mississippi and adhered to the regulations of the National Institutes of Health Guide for Care and Use of Laboratory Animals.

For the Elevated plus-maze (EPM) study, the EPM apparatus consisted of two open arms (30×5 cm) and two enclosed arms (30×5 cm, walls 15 cm high) which extended from a common central platform (5×5 cm). The configuration formed the shape of a plus-sign with comparable arms arranged opposite one another. The apparatus was elevated 50 cm above the floor level.

Animals (n=6-10/group) were acclimatized for 30 min in the EPM room before pterostilbene or diazepam treatment. While pterostilbene was given orally, diazepam was administered intraperitoneally (i.p.). Upon completion of pterostilbene or diazepam administration by oral gavage and i.p., respectively, mice were allowed to stay in the same room for 60 min and 30 min, respectively, prior to the EPM trial. Thereafter, mice were placed individually in the center of the apparatus facing an open arm, and allowed to freely explore for 5 min. The Traveled Distance in Open Arms (TDOA), the Traveled Distance in Enclosed Arms (TDEA); Permanence Time in the Open Arms (PTOA), Permanence Time in the Enclosed Arms (PTEA), Number of Entries in the Open Arms (NEOA) and Number of Entries in the Enclosed Arms (NEEA) were measured; i.e., the percentage of distance traveled, and time spent on both open and enclosed arms, and the number of open-end enclosed-arm entries were quantified using a computer-assisted video tracking system (San Diego Instruments, CA, USA). The maze was wiped clean with glass cleaner and dried after each trial. An arm entry was recorded when all four paws of the mouse were in the arm. The percentage of time spent in the open arms and the number of open arm entries are considered to be critical determinants, and pure measures of anxiety (Hogg, supra).

Figure 2:
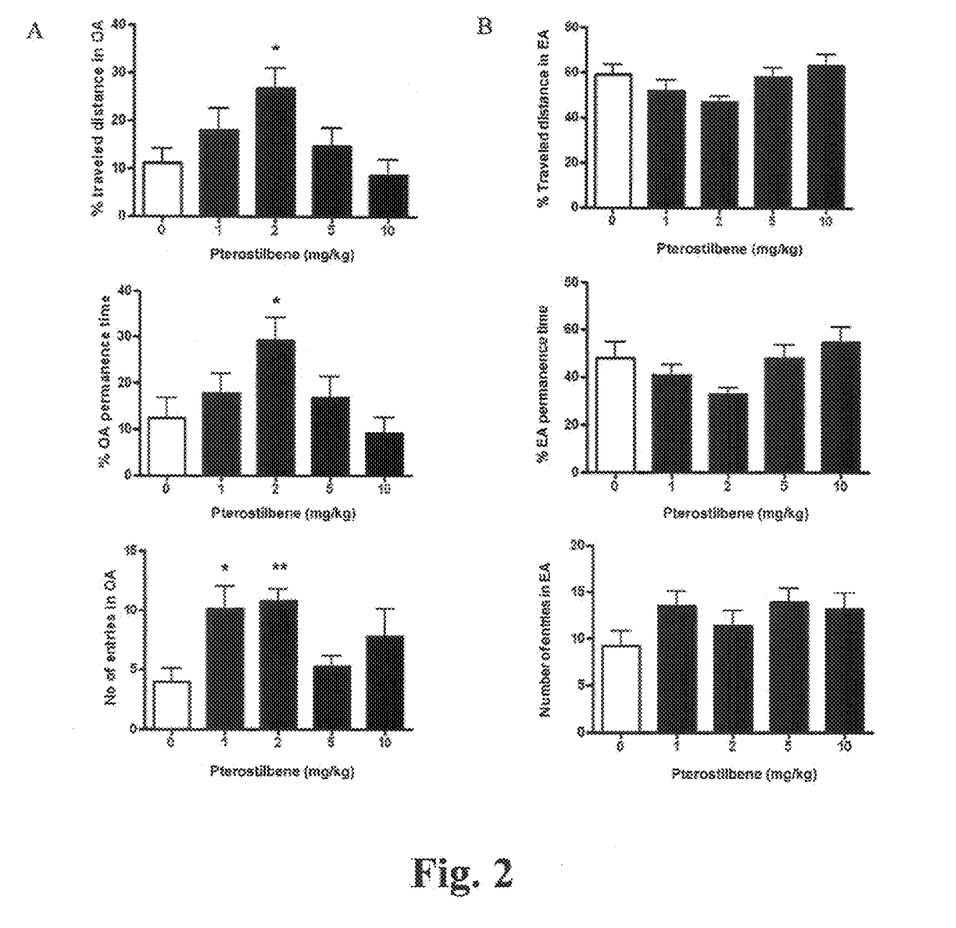
FIGS. 2A and 2B show the effect of oral administration of pterostilbene on behavior in the elevated plus-maze (EPM) test. Male Swiss Webster mice were injected with vehicle or pterostilbene (1-10 mg/kg) by oral gavage 60 min before testing on the EPM for 5 min. Percentage of distance traveled, percentage of time spent, and number of entries in open (FIG. 2A) and enclosed (FIG. 2B) arms, OA and EA respectively, were measured. Each column represents the mean±SEM. n=6-10 per dose. *$p<0.05$, **$p<0.01$ compared to vehicle control (one-way ANOVA followed by Dunnett's test).

Here, for the first time, we show that pterostilbene (FIG. 1) dose-dependently exhibited anxiolytic-like action in EPM. The anxiolytic action was apparent at 1 mg/kg dose of the compound, reached the maximum at 2 mg/kg, and then declined at 5, and 10 mg/kg doses. When compared to control (0 mg/kg), pterostilbene significantly increased all the parameters correlated with anxiolytic-like effects: % traveled distance in open arms (TDOA) [$F(4,43)=3.056$, $p<0.05$], % permanence time in open arms (PTOA) [$F(4, 43)=2.657$, $p<0.05$], and number of entries in open arms (NEOA) [$F(4,43)=4.257$, $p<0.01$] (FIG. 2A). Also, pterostilbene showed a decreasing trend of the parameters in enclosed arms which are correlated with anxiety such as % traveled distance in enclosed arms (TDEA), % permanence time in enclosed arms (PTEA), and number of entries in the enclosed arms (NEEA) (FIG. 2B). Thus, the maximal anxiolytic activity was obtained with the dose of 2 mg/kg. The highest dose of 10 mg/kg was ineffective.

Traditionally, arm entries and exits are counted when an animal crosses the threshold to an arm (Hogg, supra). In our experiments, an arm entry was recorded when all four paws of the mouse were in the arm. It is, therefore, possible for the mice to be in the central square zone which is neither the open nor the enclosed sections of the maze. In our recordings, we considered the central zone to be separate from both the open and enclosed arms, and thereby, yielding results which are more precise and indicative of genuine anxiolytic effect.

Example 3

Effect of Pterostilbene in Murine Spontaneous Motor Activity Behavioral Study

To measure spontaneous motor activity, adult Swiss Webster mice (n=8-10/group) were administered with pterostilbene by oral gavage. Each mouse was then placed in the locomotor chamber and acclimated in the Plexiglas enclosure for 30 min. After the 30 min acclimation period, locomotor activity was measured for 30 min using an automated activity monitoring system (San Diego Instruments, CA, USA). Total activity was expressed as the total number of interruptions of 16 cell photobeams per chamber.

Figure 3:
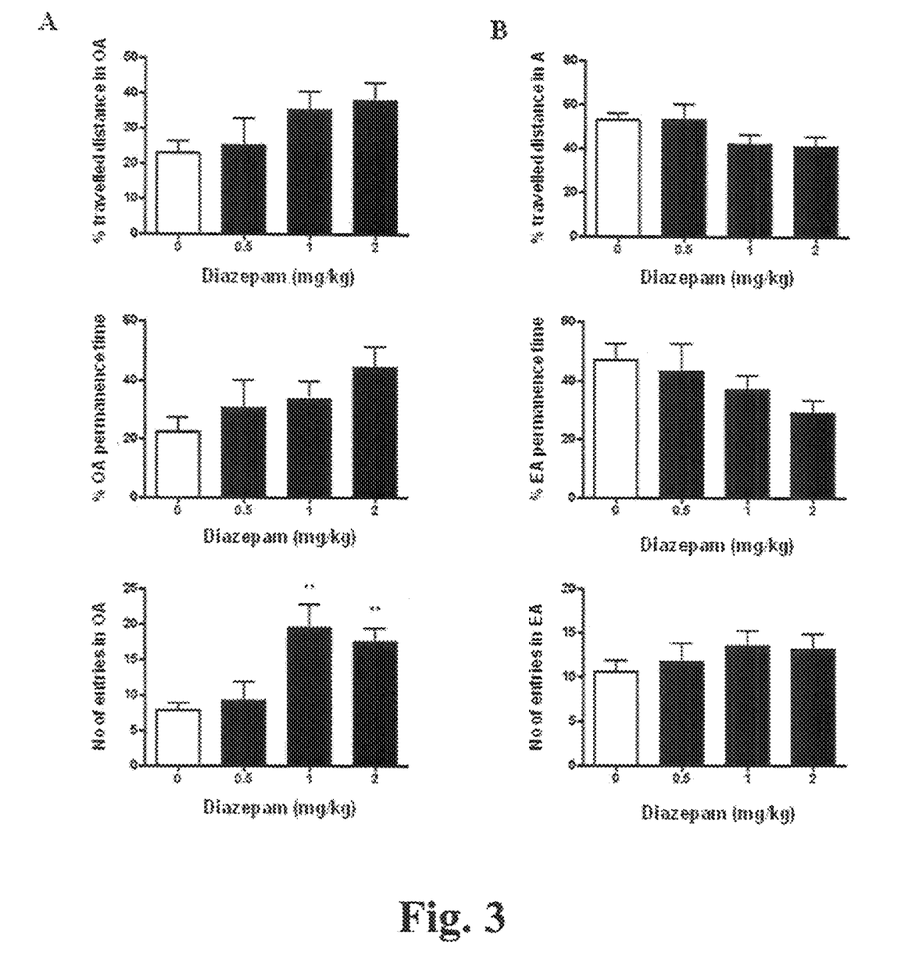
FIG. 3 depicts the effect of intraperitoneal (i.p) administration of diazepam on behavior in the elevated plus-maze test. Male Swiss Webster mice were injected with vehicle or diazepam (0.5-2 mg/kg) by i.p. 30 min before testing on the EPM for 5 min. Percentage of distance traveled, percentage of time spent, and number of entries in open (FIG. 3A) and enclosed (FIG. 3B) arms, OA and EA respectively, were measured. Each column represents the mean ±SEM. n=6-10 per dose. **p<0.01 compared to vehicle control (one-way ANOVA followed by Dunnett's test).

To illustrate the effect on spontaneous motor activity, we measured the locomotor activity of the animals after treatment with pterostilbene with doses ranging between 1 and 10 mg/kg (FIG. 3). One-way ANOVA indicated no significant effect of drug treatment on locomotor activity. Post hoc comparison showed that spontaneous motor activity was not affected by the maximal anxiolytic dose of pterostilbene. The highest dose also didn't have any effect on the locomotor activity of the animals.

Example 4

Western Blot Analysis: Blood and Tissue

After the EPM session, blood samples were taken from each mouse by submandibular vein puncture in heparinized blood collection vials. Mice were then sacrificed and brains quickly removed. Their prefrontal cortex (PFC) and hippocampus were dissected out on ice, and immediately frozen in liquid nitrogen and stored at −80° C. until further processing. Blood samples were centrifuged at 2000 rpm at 4° C. for 20 min to get the plasma as supernatant. The plasma samples were stored at −80° C. until used.

Western blot analysis of mouse brain hippocampus was performed as described previously (Al Rahim et al. 2009. *Biochemistry* 48:7713-7721) with minor modification. In brief, frozen hippocampi were homogenized in ice-cold homogenization buffer [50 mM Tris-HCl (pH 7.5), 150 mM NaCl, 5 mM EDTA, 1% NP-40, 0.5 mM DTT, and 10 μl of Halt Protease & Phosphates Inhibitor Cocktail (Thermo Scientific, IL, USA) per mL of buffer]. The homogenate was centrifuged at 12,000 g at 4° C. for 10 min. The supernatant was collected, supplemented with sample buffer, and boiled at 95° C. for 5 min. The prepared sample was thus ready for Western blot experiments. An equal amount of protein (30 μg) was subjected to SDS-polyacrylamide gel electrophoresis (12% gels), and the blotted membrane was blocked in TBST buffer containing 5% skim milk for 1 h at room temperature. The membrane was then incubated with anti-phospho-ERK (Thr 202/Tyr 204, Cell Signaling Technologies, USA) antibody. The other gel was run with the same sample, and the membrane was incubated with anti-beta-actin antibody (Cell signaling Technologies, USA). The expression level of phospho-Akt in hippocampus was checked by using anti-phospho-Akt (Ser 473, Cell signaling Technologies, USA) antibody followed by re-probing with anti-β-actin antibody (Cell signaling Technologies, USA). Bound antibodies were detected with horseradish peroxidase-linked anti-rabbit antibody (Cell Signaling Technologies, USA) and developed using VersaDoc imaging system (Bio-Rad, USA). The relevant immunoreactive bands were quantified using Quantity One 1-D Analysis Software (Bio- Rad, USA). To evaluate ERK activation, the phospho-ERK levels were normalized to that of β-actin.

Figure 4:
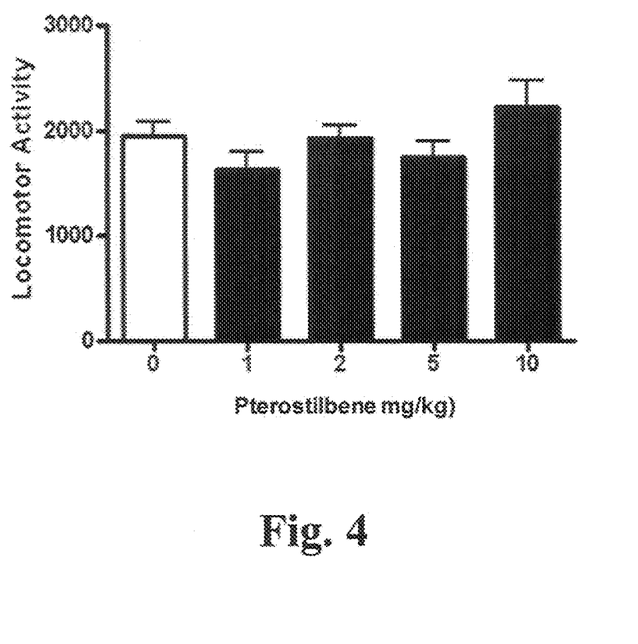
FIG. 4 depicts the effect of oral administration of pterostilbene on mouse locomotor activity. Male Swiss Webster mice were injected with vehicle or pterostilbene (1-10 mg/kg) by oral gavage 60 min before testing on the elevated plus-maze for 5 min. Spontaneous activity was evaluated in terms of the total number of interruptions per chamber. Each column represents the mean±SEM. n=8-10 per dose.

Considering that the levels of pERK increase significantly during anxiety, and that inhibition of the ERK signal transduction pathway might play a role in producing anxiolysis (Ailing et al., 2008), we next determined the phosphorylation state of ERK1/2 in homogenates from the hippocampus. Western blot analysis revealed a decrease in both ERK1 [$F(4, 15)$=12.49, $p<0.001$] and ERK2 [$F(4, 15)$=3.024, $p<0.05$] phosphorylation in hippocampal homogenates from mice treated with 1 and 2 mg/kg of pterostilbene (FIGS. 4,A and B). The doses 5 and 10 mg/kg, which did not show any anxiolytic-like effect in EPM showed no significant effects on the phosphorylation of ERKs. It is also worth mentioning that the decrease in ERK1 phosphorylation was much more marked than that of ERK2. There was no significant change in the phosphorylation of ERKs in the prefrontal cortex of mice treated with pterostilbene (data not shown).

Figure 5:
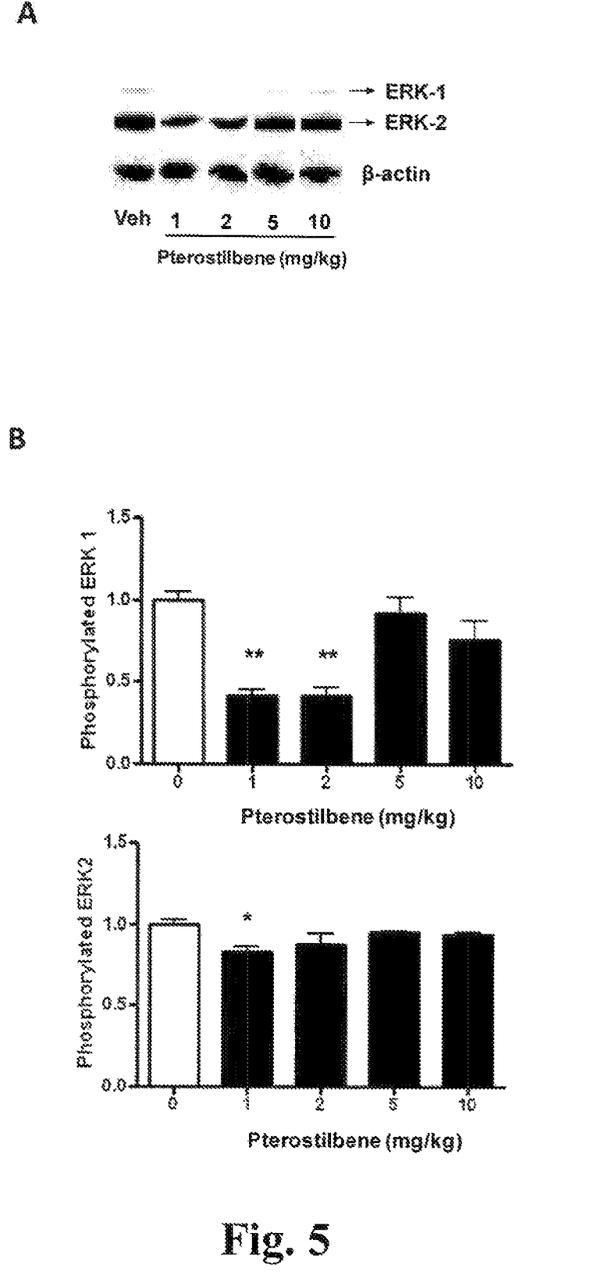
Figure 6:
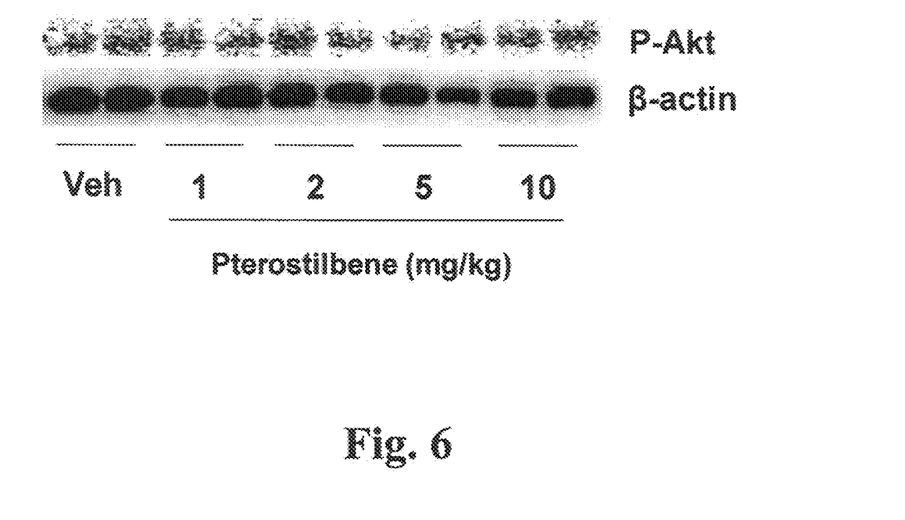
FIG. 6 depicts the effect of oral administration of pterostilbene on phosphorylation of Akt in the hippocampus. Representative data on phosphorylated ERK1/2 levels for mice sacrificed immediately after elevated plus-maze test. Following probing with the antibody specific to phosphorylated Akt (Ser 473), blots were re-probed with anti-β-actin antibody.

To determine whether these effects were a result of an indiscriminate reduction in the phosphorylated state of other kinases by the central actions of pterostilbene, we measured the phosphorylated Akt level in the hippocampus. In contrast to the marked reduction in ERKs phosphorylation, the phosphorylation state of Akt was found almost unaltered in hippocampus of mice treated with the compound ranging 1 to 10 mg/kg (FIG. 5).

Example 5

Analysis of Pterostilbene in Plasma and Hippocampus and PFC by Gas Chromatography-Mass Spectrometry (GC-MS)

Plasma were kept at −80° C., and thawed on ice prior to extraction. Plasma were treated with β-glucuronidase, to hydrolyze any glucuronidated pterostilbene, following published procedures (Remsberg et al., supra). Briefly, 50 µL plasma (from each animal) was transferred to an Eppendorf tube, and 60 µL of β-glucuronidase solution (5000 U/mL potassium phosphate buffer, 75 mM, pH 6.8 at 37° C.) was added. The mixture was vortex-mixed then incubated at 37° C. while shaking at 750 rpm for 20 hrs. Thereafter, ice-cold HPLC grade acetonitrile was added, vortex-mixed, and centrifuged for 5 min at 5000 rpm, 4° C. The supernatant was collected, and dried under a stream of nitrogen. The dried supernatant was used for GC-MS analysis.

Hippocampus tissues were kept at −80° C. until time of extraction. Hippocampus (left and right) from 2-3 animals was combined in an Eppendorf tube, and processed as one sample. To the tube was added 200 µL phosphate buffer (0.2M $NaH_2PO_4$:0.2M $Na_2HPO_4$, and the tissues were homogenized manually for 2 minutes. To 100 µl aliquot, 50 µL β-glucuronidase (5000 U/mL potassium phosphate buffer) was added. The mixture was vortex-mixed, and incubated (37° C., 20 hours) while shaking (750 rpm). The samples were then centrifuged (15 min, 7000 g, 4° C.). The supernatant was collected and partitioned with ethyl acetate (200 µL, twice). The ethyl acetate layers were combined, dried under a stream of nitrogen, and used for GC-MS analysis. Extraction of the prefrontal cortex (PFC) was performed in the same manner as the hippocampus; PFC tissues from three animals were combined and treated as one sample.

The nitrogen-dried samples (plasma and brain tissue extracts) were treated with 30 µL of a 1:1 mixture of N,O-bis[trimethylsilyl]trifluoroacetamide and dimethylformamide (Pierce Biotechnology, Inc., Rockford, Ill.) and heated at 70° C. for 40 min. The derivatized samples were analyzed for levels of pterostilbene using a JEOL GCMate II Instrument (JEOL USA Inc., Peabody, Mass.) equipped with a J&W DB-5 capillary column (0.25 mm internal diameter, 0.25 µm film thickness, and 30 m length; Agilent Technologies, Foster City, Calif.). The GC temperature program was: initial 190° C., increased to 240° C. at 20° C./min rate, increased to 280 ° C. at the rate of 2.5° C./min, then finally increased to 300° C. at the rate of 30° C./min and held at this temperature for 0.5 min. The carrier gas was ultrahigh purity helium, at 1 mL/min flow rate. The injection port, GC-MS interface, and ionization chamber were kept at 250, 230, and 230° C., respectively. The volume of injection was 2 µL (splitless injection). The mass spectrum was acquired in the positive, selected ion-monitoring mode (m/z 328, 313, and 297); electron impact 70 eV. GC-MS analyses were in duplicates. The retention time of pterostilbene was 10.2 min. Quantitation of pterostilbene was done using an external standard of a synthetic sample of pterostilbene previously characterized for structure and purity.

The plasma level of pterostilbene at 1 mg/kg dose was found to be 10.08±6.67 ng/mL, and increased correspondingly with dose reaching 130.26±40.25 rig/mL at 10 mg/kg (Table 1). The level of pterostilbene in the hippocampus tissues at 1 mg/kg dose were detectable but below the limit of quantitation (0.0840 ng). At 2, 5, and 10 mg/kg doses, the levels were quantifiable, and ranged from 0.2627-1.1217 ng/hippocampus (Table 2). Only trace levels of pterostilbene (unquantifiable) were found in the pre-frontal cortex tissues for all the doses administered.

TABLE 1

Levels of pterostilbene in the plasma.

| Dose (mg/kg BW) | n | Pterostilbene (ng/mL ± SD) |
| --- | --- | --- |
| 1 | 5 | 10.0887 ± 6.6699 |
| 2 | 9 | 27.0256 ± 7.2672 |
| 5 | 7 | 72.0104 ± 19.03902 |
| 10 | 7 | 130.2651 ± 40.2558 |

TABLE 2

Levels of pterostilbene in the hippocampus.

| Dose (mg/kgBW)[a] | n[b] | Pterostilbene (ng/hippocampus ± SD) |
| --- | --- | --- |
| 2 | 2 | 0.2627 ± 0.0230 |
| 5 | 2 | 0.5314 ± 0.1830 |
| 10 | 2 | 1.1217 ± 0.1322 |

[a]At 1 mg/kg dose, pterostilbene levels are below the limit of quantitation (0.0840 ng).
[b]A sample consists of combined hippocampal tissues from 2-3 animals.

All publications and patents mentioned in this specification are herein incorporated by reference to the same extent as if each individual publication or patent was specifically and individually indicated to be incorporated by reference.

It is understood that the foregoing detailed description is given merely by way of illustration and that modifications and variations may be made therein without departing from the spirit and scope of the invention.

We claim:

1. A method for treating an anxiety disorder in a subject in need thereof, comprising administering to the subject a pharmaceutical or nutraceutical composition comprising a therapeutically effective amount of pterostilbene wherein a therapeutic anxiolytic effect results after a single administration of said therapeutically effective amount of pterostilbene and said therapeutic anxiolytic effect is comparable to the therapeutic anxiolytic effect of Diazepam, a positive anxiolytic control, and is substantially free of sedative side effects.

2. The method of claim 1 wherein said therapeutic anxiolytic effect resulting from the administration of said therapeutically effective amount of pterostilbene manifests as a dose-dependent response as compared to a negative control.

3. The method of claim 1 wherein said administration of said therapeutically effective amount of pterostilbene results in a marked reduction of ERK1 levels in the hippocampus and said reduction of ERK1 activity correlates with a therapeutic anxiolytic effect.

4. The method of claim 1 wherein said subject is a mammal suffering from an anxiety disorder.

5. The method of claim 1 wherein said subject is a human suffering from an anxiety disorder.

6. The method of claim 1 wherein said amount is a total amount and said total amount is based on the body weight and the body surface area of said mammal.

7. The method of claim 6 wherein said amount is a total amount of about 10 mg/day to about 100 mg/day.

8. The method of claim 1 wherein said nutraceutical composition is a food or beverage or a supplement composition for a food or beverage.

9. The method of claim 8 wherein said amount is present in an amount of about 10 mg/day to about 100 mg/day.

* * * * *